(12) United States Patent
Tso et al.

(10) Patent No.: US 6,613,560 B1
(45) Date of Patent: Sep. 2, 2003

(54) PCR MICROREACTOR FOR AMPLIFYING DNA USING MICROQUANTITIES OF SAMPLE FLUID

(75) Inventors: Jacqueline Tso, Fremont, CA (US); Sally A. Swedberg, Palo Alto, CA (US); Paul K. Wolber, Los Altos, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/502,597

(22) Filed: Feb. 11, 2000

Related U.S. Application Data (63) Continuation-in-part of application No. 08/656,281, filed on Apr. 27, 1998, now Pat. No. 6,033,628, which is a continuation-in-part of application No. 08/482,245, filed on Jun. 7, 1995, now Pat. No. 5,658,413, which is a continuation-in-part of application No. 08/326,111, filed on Oct. 19, 1994, now Pat. No. 5,500,071.

(51) Int. Cl.[7] .............................. C12M 1/40; C12P 19/34
(52) U.S. Cl. ....................... 435/287.2; 435/6; 435/91.2; 435/288.5
(58) Field of Search ........................... 435/287.2, 288.5, 435/288.7, 303.1, 6, 91.2; 204/451, 601

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,800,159 A | | 1/1989 | Mullis et al. |
| 4,891,120 A | | 1/1990 | Sethi et al. |
| 4,908,112 A | | 3/1990 | Pace |
| 4,965,188 A | | 10/1990 | Mullis et al. |
| 5,132,012 A | | 7/1992 | Miura et al. |
| 5,156,810 A | * | 10/1992 | Ribi |
| 5,194,133 A | | 3/1993 | Clark et al. |
| 5,252,294 A | * | 10/1993 | Kroy et al. |
| 5,291,226 A | | 3/1994 | Schantz et al. |
| 5,305,015 A | | 4/1994 | Schantz et al. |
| 5,333,675 A | | 8/1994 | Mullis et al. |
| 5,587,128 A | * | 12/1996 | Wilding et al. |
| 5,641,400 A | * | 6/1997 | Kaltenbach et al. |
| 5,656,493 A | | 8/1997 | Mullis et al. |
| 5,677,196 A | * | 10/1997 | Herron et al. |
| 5,849,208 A | * | 12/1998 | Hayes et al. |
| 5,948,673 A | * | 9/1999 | Cottingham |
| 6,033,628 A | * | 3/2000 | Kaltenbach et al. |
| 6,255,083 B1 | * | 7/2001 | Williams |

OTHER PUBLICATIONS

Fan et al. (1994), "Micromachining of Capillary Electrophoresis Injectors and Separators on Glass Chips and Evaluation of Flow at Capillary Intersections," *Analytical Chemistry* 66(1):177–184.

Harrison et al. (1993), "Towards Miniaturized Electrophoresis and Chemical Analysis Systems on Silicon: An Alternative to Chemical Sensors," *Sensors and Actuators B*, 10(2):107–116.

Manz et al. (1990), "Design of an Open–Tabular–Column Liquid Chromatograph Using Silicon Chip Technology," *Sensors and Actuators B1*:249–255.

Manz et al. (1991), Micromachining of Monocrystalline Silicon and Glass for Chemical Analysis Systems, *Trends in Analytical Chemistry* 10(5):144–149.

Manz et al. (1993), "Planar Chips Technology for Miniaturization of Separation Systems: A Developing Perspective in Chemical Monitoring," *Adv. in Chrom.* 33:1–66.

* cited by examiner

*Primary Examiner*—William H. Beisner (57) ABSTRACT

A microanalytical device is provided for conducting chemical processes using small amounts of fluid. The devices include microstructures, e.g., microcavities, microchannels and the like, that are laser ablated or otherwise formed in a support substrate, and can be used in a variety of chemical and biochemical methods, including chromatographic, electrophoretic and electrochromatographic separations, screening and diagnostics, and chemical and biochemical synthesis. The devices are formed from a material that is thermally and chemically stable and resistant to biofouling, significantly reducing electroosmotic flow and unwanted adsorption of solute. Preferred materials are polymeric.

52 Claims, 5 Drawing Sheets

PCR MICROREACTOR FOR AMPLIFYING DNA USING MICROQUANTITIES OF SAMPLE FLUID

CROSS-REFERENCE TO RELATED APPLICATIONS

This application is a continuation-in-part of U.S. patent application Ser. No. 08/656,281, filed Apr. 27, 1998, now U.S. Pat. No. 6,033,628 which was a continuation-in-part of U.S. patent application Ser. No. 08/482,245, filed Jun. 7, 1995, now U.S. Pat. No. 5,658,413, which was a continuation-in-part of U.S. patent application Ser. No. 08/326,111, filed Oct. 19, 1994, now U.S. Pat. No. 5,500,071, each of which is incorporated by reference herein.

TECHNICAL FIELD

This invention relates generally to the field of miniaturized devices for conducting chemical and biochemical processes, and more particularly relates to a novel microreactor for conducting DNA amplification using the polymerase chain reaction, or "PCR."

BACKGROUND

In sample analysis instrumentation, smaller dimensions generally result in improved performance characteristics and at the same time result in reduced production and analysis costs. Miniaturized separation systems, for example, provide more effective system design, result in lower overhead, and enable increased speed of analysis, decreased sample and solvent consumption and the possibility of increased detection efficiency.

Accordingly, several approaches have been developed in connection with miniaturization of devices for use in chemical analysis, particularly in micro-column liquid chromatography ($\mu$LC), wherein columns with diameters of 100 to 200 microns are used, in capillary electrophoresis (CE), wherein electrophoretic separation is conducted in capillaries on the order of 25 to 100 microns in diameter, and in microchannel electrophoresis (MCE), wherein electrophoresis is carried out within a microchannel on a substantially planar substrate. The conventional approach in miniaturization technology as applied to CE and $\mu$LC involves use of a silicon-containing material, i.e., a capillary fabricated from fused silica, quartz or glass. With MCE, an attractive method that is useful in conjunction with high throughput applications and enables reduction in overall system size relative to CE, miniaturized devices have been fabricated by silicon micromachining or lithographic techniques, e.g., microlithography, molding and etching. See, for example, Fan et al. (1994) *Anal. Chem.* 66(1):177–184; Manz et al., (1993) *Adv. in Chrom.* 33:1–66; Harrison et al. (1993), *Sens. Actuators, B* B10(2):107–116; Manz et at. (1991), *Trends Anal. Chem.* 10(5):144–149; and Manz et at. (1990) *Sensors and Actuators B (Chemical)* B1(1–6):249–255. The use of micromachining techniques to fabricate miniaturized separation systems in silicon provides the practical benefit of enabling mass production of such systems, and there are a number of techniques that have now been developed by the microelectronics industry for fabricating microstructures from silicon substrates. Examples of such micromachining techniques to produce miniaturized separation devices on silicon or borosilicate glass chips can be found in U.S. Pat. Nos. 5,194,133 to Clark et al., 5,132,012 to Miura et al., 4,908,112 to Pace, and 4,891,120 to Sethi et al.

Use of silicon-containing substrates such as fused silica, quartz and glass in microanalytical devices is problematic in a number of ways. For example, silicon dioxide substrates have high energy surfaces and strongly adsorb many compounds, most notably bases. Silicon dioxide materials also dissolve to an appreciable extent when used with basic solutions. Furthermore, when used in electrophoretic applications, the internal surface of a silica capillary or microchannel will be negatively charged at basic pH as a result of deprotonation of surface silanol groups (i.e., they are in the form of anionic, Si—O$^-$, groups). The surface charge on the interior of the capillary or microchannel not only exacerbates the problem of unwanted adsorption of solute, but also modulates the velocity of electroosmotic flow (also termed "electroendoosmotic flow" or EOF) on an unmodified surface, in turn affecting the sensitivity and reproducibility of the chemical analysis conducted. (That is, the EOF velocity is a function of zeta potential $\zeta$, which is essentially determined by surface charge.) Microfabrication using silicon per se is similarly problematic insofar as a silica surface will form on a silicon substrate under even mildly oxidizing conditions.

For the foregoing reasons it would be desirable to fabricate microanalytical and other miniaturized devices from materials that are not silicon-based, e.g., using inexpensive and readily available polymeric materials. It would also be desirable to extend the utility of microdevices beyond electrophoretic and chromatographic separation techniques to other types of chemical processes, processes that may involve high temperatures, extremes of pH, harsh reagents, or the like. The present invention provides such microanalytical devices.

The area with which the present invention is concerned is in bioanalysis. An important technique currently used in bioanalysis and in the emerging field of genomics is the polymerase chain reaction (PCR) amplification of DNA. As a result of this powerful tool, it is possible to start with otherwise undetectable amounts of DNA and create ample amounts of the material for subsequent analysis. The technique is described in U.S. Pat. No. 4,683,195 to Mullis et al. and related U.S. Pat. Nos. 4,683,202, 4,800,159 and 4,965,188 to Mullis et al. Automated systems for performing PCR are known, as described, for example, in U.S. Pat. Nos. 5,333,675 and 5,656,493 to Mullis et al. PCR uses a repetitive series of steps to create copies of polynucleotide sequences located between two initiating ("primer") sequences. Starting with a template, two primer sequences (usually about 15–30 nucleotides in length), PCR buffer, free deoxynucloside tri-phosphates (dNTPs), and thermostable DNA polymerase (commonly Taq polymerase), one mixes these components, and then heats to separate the double-stranded DNA. A subsequent cooling step allows the primers to anneal to complementary sequences on single-stranded DNA molecules containing the sequence to be amplified. Replication of the target sequence is then accomplished by the DNA polymerase which produces a strand of DNA that is complementary to the template. Repetition of this process doubles the number of copies of the sequence of interest, and multiple cycles increase the number of copies exponentially.

Since PCR requires repeated cycling between higher and lower temperatures, PCR devices must be fabricated from materials capable of withstanding such temperature changes. The materials must be mechanically and chemically stable at high temperatures, and capable of withstanding repeated temperature changes without mechanical degradation. Furthermore, the materials must be compatible with the PCR reaction itself, and not inhibit the polymerase or bind DNA.

To date, however, there remain many problems with performing PCR in microdevices. One problem involves the low thermal stability of many materials. That is, many types of materials, e.g., polymeric materials, cannot withstand the cycling temperatures used in PCR, typically in the range of about 37° C. to 90° C., without significant or complete loss of mechanical integrity. In addition, contaminants may be present on or leach out of a substrate surface, affecting the precise balance of appropriate ingredients (metal ions, salts, buffering systems, oligonucleotides, primers, and polymerases) required for PCR, in turn resulting in unsuccessful amplification reactions. Also, the polymerase enzyme or any of the components involved in the PCR reaction may bind to or become adsorbed on a microchannel surface. Contact between the polymerase and a substrate surface will generally result in irreversible denaturation. These types of "biofouling" are especially problematic with capillaries or microchannels of micron or submicron dimensions because of the very high surface area to volume ratio.

SUMMARY OF THE INVENTION

The present invention addresses the aforementioned needs in the art, and provides a PCR microreactor for amplifying DNA using microquantities of sample fluid. In its simplest embodiment, the PCR microreactor comprises: a reaction chamber defined by two or more interior surfaces, a means for introducing PCR reaction components into the chamber, a means for removing the PCR reaction product from the chamber, and a means for controlling the temperature of the reaction chamber, wherein the device is fabricated from a material that is thermally, chemically and mechanically stable under the conditions at which a PCR reaction is conducted, and employs a reaction chamber adapted to contain in the range of approximately 1 µl to 500 µl of fluid. Preferred materials are those that exhibit reduced adsorption of solute, e.g., biomolecules such as proteins, nucleic acids, etc., and can be modified, coated or otherwise treated so as to optimize electroosmotic flow.

A second embodiment of the invention the PCR microreactor comprises:

a substrate having first and second substantially planar opposing surfaces, with a cavity and at least one microchannel formed in the first planar surface, wherein the cavity serves as a reaction zone that is in fluid communication with each microchannel;

a cover plate arranged over the first planar surface, which in combination with the cavity defines a reaction chamber, and with each microchannel defining a microcolumn; and at least one inlet port and at least one outlet port communicating directly or indirectly with the reaction chamber, enabling the passage of fluid from an external source into and through the reaction chamber, wherein the substrate and the cover plate are comprised of a material that is thermally and chemically stable and resistant to biofouling.

An additional embodiment of the invention presents a method for conducting the polymerase chain reaction (PCR) to amplify DNA in a sample which comprises heating the sample to separate double-stranded DNA into single-stranded DNA, cooling the sample so as to allow hybridization of primer oligonucleotides to the single-stranded DNA, replicating the DNA using a DNA polymerase, and repeating the aforementioned steps to achieve the desired degree of amplification, wherein the PCR is conducted in a microreactor comprised of a material that is thermally, chemically and mechanically stable under the conditions at which the PCR reaction is conducted, and employs a reaction chamber adapted to contain approximately 1 µl to 500 µl of fluid.

In a further embodiment a method is presented for amplifying the quantity of a DNA molecule of interest contained in a small volume of sample fluid using the polymerase chain reaction, comprising:

(a) introducing into a microreactor up to about 10 µl of a sample fluid containing the DNA molecule of interest in double-stranded form, a first and a second primer molecule complementary to opposing strands of the DNA molecule, a thermostable DNA polymerase, free deoxynucleoside triphosphates and PCR buffer, the microreactor comprising a substrate having first and second substantially planar opposing surfaces, said substrate having a cavity formed in the first planar surface, wherein the cavity serves as a reaction zone, a cover plate arranged over the first planar surface, said cover plate in combination with the cavity defining a reaction chamber, and at least one inlet port and at least one outlet port in fluid communication with the reaction chamber, said ports enabling the passage of sample fluid from an external source into and through the reaction chamber, thereby defining a fluid flow path, wherein the substrate and the cover plate are comprised of a material that is thermally stable and resistant to biofouling;

(b) applying a motive force to the device to move the sample fluid along the flow path into the reaction chamber;

(c) heating the sample fluid in the reaction chamber to separate the double-stranded DNA into single-stranded DNA;

(d) cooling the sample so as to allow hybridization of the primer molecules to opposing strands of the single-stranded DNA and replication of the single-stranded DNA by the DNA polymerase; and (e) repeating steps (c) and (d) to achieve the desired degree of amplification.

In a still further embodiment of the invention, a method is presented for amplifying the quantity of a DNA molecule of interest contained in a small volume of sample fluid using the polymerase chain reaction, comprising:

(a) introducing into the microreactor of the second embodiment of the invention up to bout 10 µl of a sample fluid containing the DNA molecule of interest in double-stranded form, first and a second primer molecule complementary to opposing strands of the DNA molecule, a hermostable DNA polymerase, free deoxynucleoside triphosphates and PCR buffer, (b) applying a motive force to the device to move the sample fluid along the flow path into the reaction chamber;

(c) heating the sample fluid in the reaction chamber to separate the double-stranded DNA to single-stranded DNA;

(d) cooling the sample so as to allow hybridization of the primer molecules to opposing strands of the single-stranded DNA and replication of the single-stranded DNA by the DNA polymerase; and (e) repeating steps (c) and (d) to achieve the desired degree of amplification.

DETAILED DESCRIPTION OF THE INVENTION

Before the invention is described in detail, it is to be understood that unless otherwise indicated this invention is not limited to particular materials, components or manufacturing processes, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a material" includes mixtures of materials, reference to "a reaction chamber" includes multiple reaction chambers, and the like.

In this specification and in the claims which follow, reference will be made to a number of terms which shall be defined to have the following meanings:

The term "microreactor" refers to a device having features of micron or submicron dimensions, and which can be used in any number of chemical processes involving very small amounts of fluid (i.e., "microquantities" of fluid, in the range of about 1 $\mu$l to 500 $\mu$l, preferably in the range of about 10 $\mu$l to 200 $\mu$l). The primary process of interest is the amplification of DNA using the polymerase chain reaction. Optionally, DNA amplification may be conducted along with one or more other types of procedures. Such procedures include, but are not limited to: preparative techniques conducted prior to PCR; analysis and separation using, for example, electrophoresis (e.g., CE or MCE) or chromatography (e.g., $\mu$LC); and post-reaction purification processes. The features of the microreactors are adapted to particular uses. For example, microreactors that are used not only in PCR amplification of DNA but also in separation processes, e.g., MCE, contain microchannels (termed "microcolumns" herein when enclosed, i.e., when the cover plate is in place on the microchannel-containing substrate surface) on the order of 1 $\mu$m to 200 $\mu$m in diameter, typically 10 $\mu$m to 75 $\mu$m in diameter, and approximately 0.1 to 50 cm in length. Microreactors that are used solely in DNA amplification will contain reaction zones (termed "reaction chambers" herein when enclosed, i.e., again, when the cover plate is in place on the microchannel-containing substrate surface) having a volume of about 1 $\mu$l to about 500 $\mu$l, typically about 10 $\mu$l to 200 $\mu$l.

As used herein, the term "detection means" refers to any means, structure or configuration which allows one to interrogate a sample within a microanalytical device of the invention using analytical detection techniques well known in the art. Thus, a detection means can comprise one or more openings that communicate with, for example, a reaction chamber or microchannel, and allow an external detection device to be interfaced with the chamber or microchannel to detect an analyte therein. By the arrangement of two detection means opposite each other relative to the reaction chamber or the like, a "detection path" is formed, allowing detection of analytes passing through the reaction chamber using detection techniques well known in the art. An "optical detection path" refers to a configuration or arrangement of detection means to form a path whereby electromagnetic radiation is able to travel from an external source to a means for receiving radiation, wherein the radiation traverses the reaction chamber, microchannel, or the like. In this configuration, analytes passing through the microreactor can be detected via transmission of radiation orthogonal to the direction of fluid flow. A variety of external optical detection techniques can be readily interfaced with the present microreactors, including, but not limited to, UV/Vis, Near IR, fluorescence, refractive index (RI) and Raman techniques.

As used herein, a "transparent substance" refers to a substance capable of transmitting light of different wavelengths. Thus, a "transparent sheet" is defined as a sheet of a substance that is transmissive to specific types of radiation or particles of interest. Transparent sheets that may be employed in conjunction with the invention are formed from materials such as quartz, sapphire, diamond and fused silica, or from polymeric materials such as polystyrene and styrene-butadiene copolymer. "Optically transparent" refers to a material capable of transmitting light of wavelengths in the range of about 150 nm to 800 nm.

A "detection intersection" refers to a configuration wherein a plurality of detection means that communicate with the interior of the present microreactors converge at a particular location therein. A number of detection techniques can be simultaneously performed on a sample or separated analyte at the detection intersection. A detection intersection is formed when a plurality of detection paths cross, or when a detection means such as an aperture communicates with the separation compartment at substantially the same point as a detection path. The sample, or a separated analyte, can thus be analyzed using a combination of UV/Vis and fluorescence techniques, optical and electrochemical techniques, optical and electrical techniques, or like combinations to provide highly sensitive detection information. See, e.g., Beckers et al. (1988) *J. Chromalogr.* 452:591–600; and U.S. Pat. No. 4,927,265, to Brownlee.

The term "liquid phase analysis" is used to refer to any analysis which is carried out on a solute in the liquid phase. Accordingly, "liquid phase analysis" as used herein includes chromatographic separations, electrophoretic separations, and electrochromatographic separations. The general term "analysis" refers to characterization of a sample or identification of one or more components therein, and is distinct from a chemical or biochemical "process" in which a material is chemically or biochemically altered to produce a desired product. DNA amplification using the PCR technique represents a "process" herein, although the PCR reaction may be conducted in conjunction with an analytical process (e.g., wherein the reaction is monitored or where the reaction product is analyzed prior to removal from the device).

"Chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly, electrophoretic separations include separations performed in columns packed with gels (such as polyacrylamide, agarose and combinations thereof) as well as separations performed in solution.

"Electrochromatographic" separations refer to separations effected using a combination of electrophoretic and chromatographic techniques. Exemplary electrochromatographic separations include packed column separations using electromotive force (Knox et al. (1987) *Chromatographia* 24:135; Knox et al. (1989) *J. Liq. Chromatogr* 12:2435; Knox et al. (1991) *Chromatographia* 32:317), and micellar electrophoretic separations (Terabe et al. (1985) *Anal. Chem.* 57:834–841).

The term "injection molding" is used to refer to a process for molding plastic or nonplastic ceramic shapes by injecting a measured quantity of a molten plastic or ceramic substrate into dies (or molds). In one embodiment of the present invention, miniaturized devices can be produced using injection molding.

The term "embossing" is used to refer to a process for forming polymer, metal or ceramic shapes by bringing an embossing die into contact with a pre-existing blank of polymer, metal or ceramic. A controlled force is applied between the embossing die and the pre-existing blank of material such that the pattern and shape determined by the embossing die is pressed into the pre-existing blank of polymer, metal or ceramic. The term "hot embossing" is used to refer to a process for forming polymer, metal or ceramic shapes by bringing an embossing die into contact with a heated pre-existing blank of polymer, metal or ceramic. The pre-existing blank of material is heated such that it conforms to the embossing die as a controlled force is applied between the embossing die and the pre-existing blank. The resulting polymer, metal or ceramic shape is cooled and then removed from the embossing die.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated with high energy radiation using a synchrotron source to create desired microstructures (such as channels, ports, apertures, and micro-alignment means), thereby forming a primary template.

The term "motive force" is used to refer to any means for inducing movement of a sample along a flow path in a microreactor, and includes application of an electric potential across any portion of the microreactor, application of a pressure differential across any portion of the microreactor or any combination thereof.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Figure 1:
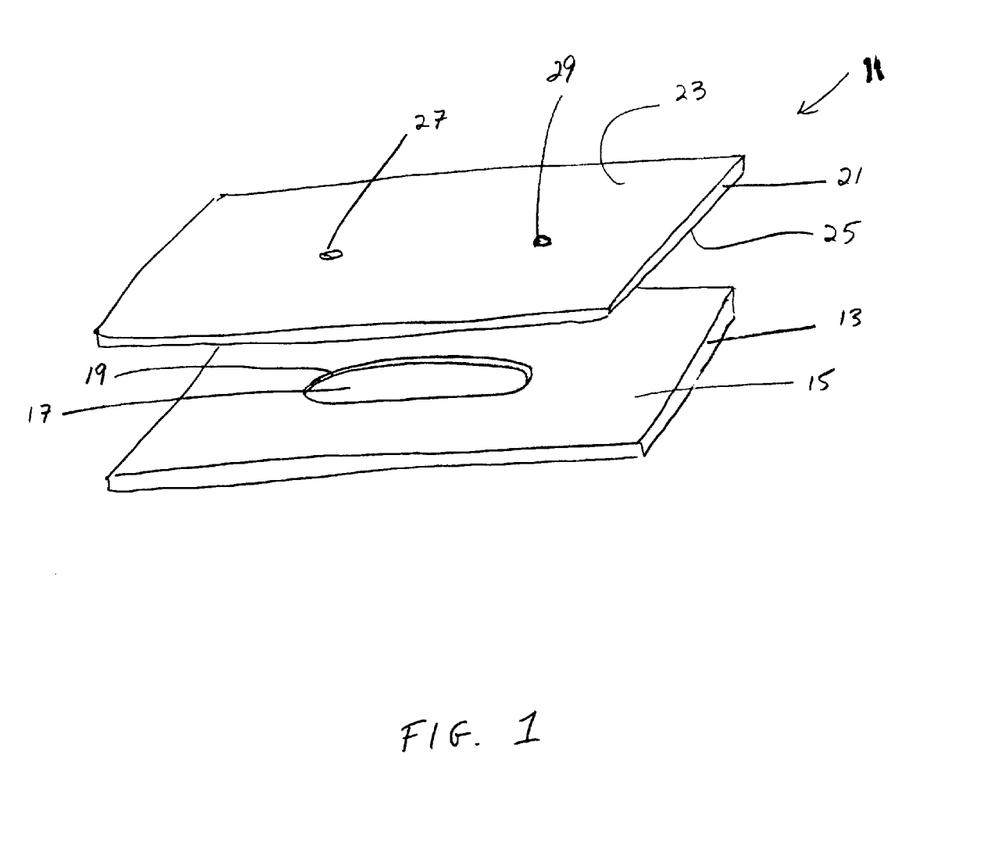
FIG. 1 is a perspective schematic view of one embodiment of a microreactor of the invention.

The Novel Microreactor:

One embodiment of the present invention is represented in FIG. 1, which schematically illustrates a microreactor that can be used in conducting a chemical process such as PCR. The device is generally represented at 11, comprising substrate 13 having a substantially planar surface 15 containing a reaction zone 17 in the form of a shallow cavity, i.e., a cavity having a depth of micron or even submicron dimensions. A cover plate 21 is shown arranged over with substrate 13. Prior to use of the device, the underside 25 of the cover plate is aligned with and placed against the surface 15 of substrate 13. The cover plate, in combination with the reaction zone 17, forms a reaction chamber in which the desired chemical process is carried out. Fluid, e.g., sample to be analyzed, analytical reagents, reactants or the like, are introduced into the reaction chamber from an external source through inlet port 27; outlet port 29 enables passage of fluid from the reaction chamber to an external receptacle. Accordingly, "closure" of the device by aligning the cover with the substrate and forming a seal therebetween results in formation of a reaction chamber into which fluids may be introduced through inlet port 27 and removed through outlet port 29. Preferably, a liquid-tight seal is formed by using pressure sealing techniques, by using external means to urge the pieces together (such as clips, tension springs or associated clamping apparatus), or by using adhesives well known in the art of bonding polymers, ceramics and the like.

Figure 2:
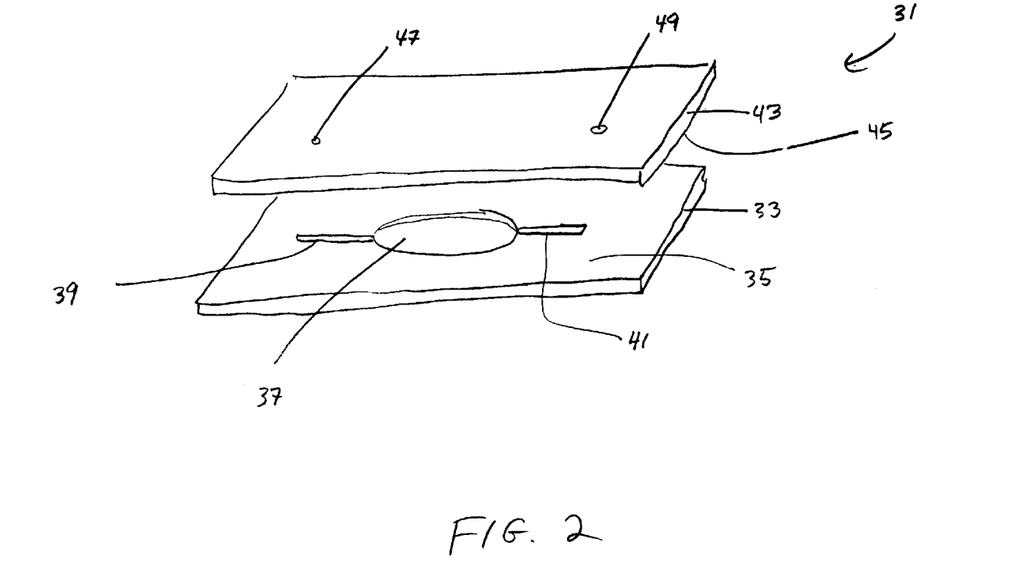
FIG. 2 is a perspective schematic view of a second embodiment of a microreactor of the invention.

In a related embodiment of the invention, as illustrated in FIG. 2, flow paths in the form of microchannels are incorporated into the substrate at either end of the reaction zone. That is, device 31 includes a substrate 33 having a substantially planar surface 35 containing a reaction zone 37, again in the form of a shallow cavity. An upstream microchannel 39 in the substrate surface is in fluid communication with the upstream region of reaction zone 37, while downstream microchannel 41 is in fluid communication with the downstream region of reaction zone 37. The cover plate 43 is shown arranged over substrate 33 with its underside 45 facing the substrate surface. The underside 45 of the cover plate is aligned with the substrate and placed against surface 35 prior to use of the device. Closure of the device in this manner, i.e., by aligning the cover with the substrate and forming a seal therebetween results in formation of a reaction chamber, an upstream microcolumn and a downstream microcolumn. Upon closure of the device, inlet port 47 in the cover plate allows introduction of fluid from an external source into the upstream microcolumn, while outlet port 49, also in the cover plate, allows removal of fluid from the downstream microcolumn. The upstream microcolumn may be used as a concentrating means to increase the concentration of a particular analyte or chemical component prior to chemical processing in the reaction chamber. Unwanted, potentially interfering sample or reaction components can also be removed using the upstream microcolumn in this way. In addition, or in the alternative, the upstream microchannel can serve as a preparatory microreactor for preparative chemical or biochemical processes prior to DNA amplification in the reaction chamber. Such preparative processes can include labeling, protein digestion, and the like. The downstream microcolumn may be used as a purification means to remove unwanted components, unreacted materials, etc. from the reaction chamber following completion of chemical processing. This may be accomplished, for example, by packing the downstream microcolumn or coating its interior surface with a material that selectively removes certain types of components from a fluid or reaction mixture.

Figure 3:
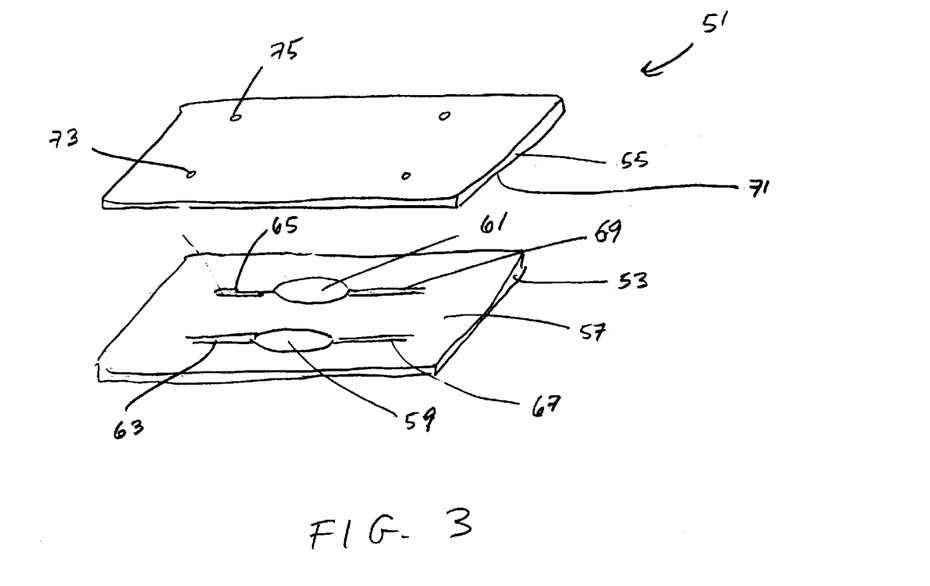
FIG. 3 is a perspective schematic view of another embodiment of a microreactor of the invention.

It will be appreciated that a microreactor of the invention may be fabricated so as to contain two or more reaction zones and optional microchannels in fluid communication therewith. An example of such a device is illustrated in FIG. 3, shown generally at 51 as comprising substrate 53 and cover plate 55 aligned therewith. The upper surface 57 of the substrate, a substantially planar surface, is provided with a first reaction zone 59 and a second reaction zone 61. A first upstream microchannel 63 is in fluid communication with the upstream region of first reaction zone 59, and a second upstream microchannel 65 is in fluid communication with the upstream region of second reaction zone 61. Correspondingly, a first downstream microchannel 67 is in fluid communication with the downstream region of first reaction zone 59, and a second downstream microchannel 69 is in fluid communication with the downstream region of second reaction zone 61. Upon closure of the device by placement of the underside 71 of cover plate 55 against substrate surface 57, two reaction chambers are formed from the first and second reaction zones 59 and 61, along with two upstream microcolumns (formed from the first and second upstream microchannels 63 and 65) and two downstream microcolumns (formed from the first and second downstream microchannels 67 and 69). A first inlet port 73 in the cover plate 55 is aligned with the upstream terminus of first upstream microchannel 63, and a second inlet port 75 is aligned with the upstream terminus of second upstream microchannel, the first and second inlet ports 73 and 75 respectively providing for introduction of fluid from an external source into the first and second upstream microcolumns. Correspondingly, a first outlet port 77 in the cover plate 55 is aligned with the downstream terminus of the first downstream microchannel, and a second outlet port 79 is aligned with the downstream terminus of the second downstream microchannel, the first and second outlet ports 77 and 79 thereby providing for removal of fluid from the first and second downstream microcolumns, respectively. In this embodiment and in the embodiments of FIGS. 1 and 2, the substrate and cover plate may be joined at one edge, such that closure of the device is effected by folding the cover plate onto the substrate. The edge may include a fold means such as a row of spaced-apart perforations, depressions or apertures, having any shape, e.g., circular, diamond, hexagonal, etc., that promote folding and thus hinge formation.

The materials used to form the substrates and cover plates in the microanalytical devices of the invention are selected with regard to physical and chemical characteristics that are desirable for a particular application. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser etching, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. Also, all device materials used should be chemically inert and physically stable with respect to any reagents with which they comes into contact, under the reaction conditions used (e.g., with respect to pH, electric fields, etc.). Since PCR involves relatively high temperatures, it is important that all materials be chemically and physically stable within the range of temperatures used. For use with optical detection means, the materials used should be optically transparent, typically transparent to wavelengths in the range of about 150 nm to 800 nm. Silicon, silicon dioxide and other silicon-containing materials should be avoided, and preferred materials are those that do not strongly adsorb solutes, e.g., proteins or other biomolecules. Suitable materials for forming the present devices include, but are not limited to, polymeric materials, ceramics (including aluminum oxide and the like), glass, metals, composites, and laminates thereof.

Polymeric materials are particularly preferred herein, and will typically be organic polymers that are either homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Polyimide is of particular interest, and has proven to be a highly desirable substrate material in a number of contexts. It has been demonstrated, for example, that polyimides exhibit low sorptive properties towards proteins, which are known to be particularly difficult to analyze in prior silicon dioxide-based systems. Polyimides are commercially available, e.g., under the tradename Kaptong®, (DuPont, Wilmington, Del.) and Upilex® (Ube Industries, Ltd., Japan).

The devices of the invention may also be fabricated from a "composite," i.e., a composition comprised of unlike materials. The composite may be a block composite, e.g., an A-B-A block composite, an A-B-C block composite, or the like. alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, available from DuPont (Wilmington, Del.), that has been co-extruded with a second, thin layer of a thermal adhesive form of polyimide known as KJ®, also available from DuPont (Wilmington, Del.).

The surfaces of the substrates and cover plates may be chemically modified to provide desirable chemical or physical properties, e.g., to reduce adsorption of molecular moieties to the interior walls of a microchannel or reaction chamber, and to reduce EOF. For example, the surface of a polymeric or ceramic substrate may be coated with or functionalized to contain electrically neutral molecular species, zwitterionic groups, hydrophilic or hydrophobic oligomers or polymers, etc. With polyimides, polyamides, and polyolefins having reactive sites or functional groups such as carboxyl, hydroxyl, amino and haloalkyl groups (e.g., polyvinyl alcohol, polyhydroxystyrene, polyacrylic acid, polyacrylonitrile, etc.), or with polymers that can be modified so as to contain such reactive sites or functional groups, it is possible to chemically bond groups to the surface that can provide a variety of desirable surface properties. An exemplary modified substrate is polyimide functionalized so as to contain surface-bound water-soluble polymers such as polyethylene oxide (PEO), which tends to reduce unwanted adsorption and minimize nonspecific binding in DNA amplification and other methodologies involving hybridization techniques. The substrate surface may also be advantageously modified using surfactants (e.g., polyethylene oxide triblock copolymers such as those available under the tradename "Pluronic," polyoxyethylene sorbitan, or "TWEEN"), natural polymers (e.g., bovine serum albumin or "BSA"), or other moieties that provide the desired surface characteristics, particularly in reducing the sorption of biomolecules such as proteins.

It should also be emphasized that different regions of a single substrate may have chemically different surfaces, e.g., the interior surface of a microchannel may comprise a first material, while the interior surface of a reaction chamber in fluid communication with that microchannel may comprise a second material. For example, the reaction chamber or chambers may have interior surfaces that are coated or functionalized, e.g., with PEO or the like, while the interior surfaces of microchannels associated with the reaction chamber(s) may not be coated or functionalized. Also, upstream and downstream microchannels may be fabricated so as to contain an ion exchange resin, a metal chelating compound, an affinity adsorbent material, or the ike, i.e., materials selected to purify a fluid or sample by removing one or more components or types of components therefrom. In this way, different components and features present in the same substrate may be used to conduct different chemical or biochemical processes, or different steps within a single chemical or biochemical process.

Fabrication:

The present microreactors can be fabricated using any convenient method, including, but not limited to, micro-molding and casting techniques, embossing methods, surface micro-machining and bulk-micromachining. The latter technique involves formation of microstructures by etching directly into a bulk material, typically using wet chemical etching or reactive ion etching ("RIE"). Surface micromachining involves fabrication from films deposited on the surface of a substrate. An exemplary surface micromachining process is known as "LIGA." See, for example, Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35–36; Ehrfeld et al. (1988), "1988 LIGA Process: Sensor Construction Techniques via x-Ray Lithography," *Tech Digest from IEEE Solid-State Sensor and Actuator Workshop*, Hilton Head, S.C.; Guckel et al. (1991) *J. Micromech. Microeng.* 1: 135–138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—i.e., diameters—on the order of microns.

A preferred technique for preparing the present microreactors is laser ablation. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation will typically involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) *Laser Focus Electro Optics*, at pp. 54–70, and in U.S. Pat. Nos. 5,291,226 and 5,305,015 to Schantz et al.

The fabrication technique that is used must provide for features of sufficiently high definition, i.e., microscale components, channels, chambers, etc., such that precise alignment—"microalignment"—of these features is possible. "Microalignment" refers to the precise and accurate alignment of laser-ablated features, including the alignment of complementary microchannels or microcompartments with each other, inlet and/or outlet ports with microcolumns or reaction chambers, detection means with microcolumns or separation compartments, detection means with other detection means, projections and mating depressions, grooves and mating ridges, and the like.

Figure 4:
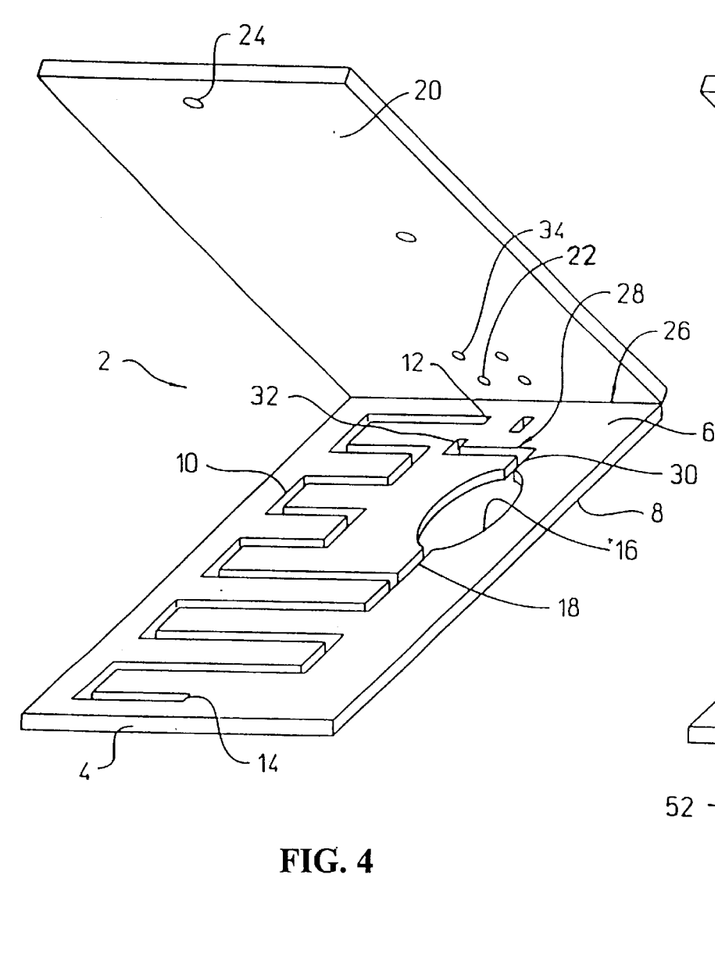
FIG. 4 is a perspective schematic view of a microreactor device of the invention which includes both a separation microchannel and an on-device reservoir.

Another embodiment of the invention is directed to a microreactor as shown in FIG. 4 that includes both a miniaturized column for conducting separation processes, e.g., electrophoretic or chromatographic separations, as well as a reservoir compartment that serves as a reaction chamber for carrying out one or more chemical or biochemical reactions. The device is shown generally at 2, comprising a selected substrate 4 having first and second substantially planar opposing surfaces indicated at 6 and 8 respectively, and fabricated from a material other than silicon or silicon dioxide. Preferably, although not necessarily, the material is UV-absorbing and laser ablatable. The substrate 4 has a microchannel 10 laser ablated or otherwise formed in first planar surface 6. It will be readily appreciated that although the microchannel 10 has been represented in a generally extended form, microchannels formed in the practice of the invention can have a variety of configurations, such as in a straight, serpentine, spiral, or any tortuous path desired, and having any number of different cross-sectional shapes, i.e., having any of a wide variety of channel geometries including semi-circular, rectangular, rhomboid, and the like, and the channels can be formed in a wide range of aspect ratios. In addition, two or more microchannels may be present in a single substrate. As indicated in FIG. 4, the microchannel 10 has an upstream terminus indicated at 12, and a downstream terminus indicated at 14.

The first planar surface 6 further includes an on-device reservoir means 16, formed from a cavity that has been laser ablated or otherwise fabricated in the first planar surface 6. The cavity can be formed in any geometry and with any aspect ratio, limited only by the overall thickness of the substrate 4, to provide a reservoir means having a desired volume. The reservoir means can be used to provide a makeup flow fluid, a fluid regulation function, or reagents for enhancing detection or separation of liquid sample constituents. The reservoir means may also serve as a reaction zone in which chemical or biochemical processes are to be conducted. Such processes, as noted earlier herein, include, but are not limited to, separation (e.g., chromatographic, electrophoretic or electrochromatographic separation), screening and diagnostics (using, e.g., hybridization or other binding means), and chemical and biochemical synthesis (e.g., DNA amplification as may be carried out using PCR). The reservoir means 16 is in fluid communication with the microchannel 10 via a fluid conducting means 18, which is formed from a duct laser ablated or otherwise fabricated in the first planar surface 6.

A cover plate 20 is arranged over the first planar surface 6 and, in combination with microchannel 10, forms an elongate separation microcolumn. Further, the cover plate 20, in combination with the reservoir means 16, forms a reservoir compartment (or when the reservoir means serves as a reaction zone, a "reaction chamber" will be formed upon placement of the cover plate on the substrate), and, likewise, in combination with the fluid conducting means 18, forms a fluid conducting compartment that communicates the reservoir compartment with the separation microcolumn. The cover plate 20 can be fixably aligned over the first planar surface 6 to form a liquid-tight separation microcolumn by using pressure sealing techniques, by using external means to urge the pieces together (such as clips, tension springs or associated clamping apparatus), or by using adhesives well known in the art of bonding polymers, ceramics and the like.

In one particular device configuration, the cover plate 20 comprises a discrete component, having a substantially planar surface capable of interfacing closely with the first planar surface 6 of the substrate 4. However, in a preferred device, the substrate and the cover plate are formed in a single, flexible substrate. Referring to FIG. 4, the flexible substrate includes first and second portions, corresponding to the substrate 4 and the cover plate 20, wherein each portion has a substantially planar interior surface. The first and second portions are separated by at least one fold means, generally indicated at 26, such that the portions can be readily folded to overlie each other. The fold means 26 can comprise a row of spaced-apart perforations in the flexible substrate, a row of spaced-apart slot-like depressions or apertures extending only partway through the flexible substrate, or the like. The perforations or depressions can have circular, diamond, hexagonal or other shapes that promote hinge formation along a predetermined straight line.

The device 2 of FIG. 4 can be formed by laser ablating a microchannel 10, a reservoir means 16 and a fluid conducting means 18 in the substrate 4. A separation microcolumn, reservoir compartment and a fluid conducting compartment are then provided by folding the flexible substrate at the fold means 26 such that the cover plate portion 20 encloses the microchannel, reservoir and fluid conducting means.

In each of the above-described devices, the cover plate 20 can also include a variety of apertures or other features which have been laser ablated or otherwise fabricated therein. Particularly, a first aperture can be arranged to communicate with the separation compartment (formed by the combination of microchannel 10 and cover plate 20) adjacent the upstream terminus 12 of the microchannel 10 to provide an inlet port 22. The inlet port enables the passage of fluid from an external source into the separation compartment when the cover plate 20 is arranged over the first planar surface 6. A second aperture can likewise be arranged to communicate with the separation microcolumn adjacent the downstream terminus 14 of the microchannel 10 to form an outlet port 24, enabling passage of fluid from the separation compartment to an external receptacle. Accordingly, a flow path extends from an upstream end of the separation microcolumn and passing to a downstream end thereof, whereby liquid phase analysis of samples can be carried out by communicating fluids from an associated source (not shown) through the inlet port, passing the fluids through the separation microcolumn, and allowing the fluids to exit the separation compartment via the outlet port.

Various means for applying a motive force along the length of the separation microcolumn, such as a pressure differential or electric potential, can be readily interfaced to the column device via the inlet and outlet ports, in any of the foregoing devices. In electrophoresis, a voltage gradient will be applied across the flow path from the inlet port to the outlet port, causing components in the flowing fluid to migrate at different rates proportional to their charge and/or mass. As will be appreciated by those skilled in the art, any convenient means may be employed for applying a voltage gradient across the flow path.

In the particular device configuration of FIG. 4, the fluid conducting means 18 enables passage of fluid from the reservoir means 16 into the separation microcolumn at a position substantially midway between the upstream and downstream termini, 12 and 14, of the microchannel 10. It is noted that although the fluid conducting means 18 has been depicted in this manner, the fluid conducting means can be arranged to communicate with the separation compartment at any position between, or at, the upstream and downstream termini thereof.

By allowing fluid communication between the fluid conducting compartment and the separation microcolumn, a number of separation or detection enhancing operations may be conducted during the course of fluid flow. For example, the reservoir means 16 can be used to deliver a liquid reagent or dye, e.g., a fluorescent indicator, which is capable of reacting with the analyte, for example to enhance the detectability thereof.

The reservoir means 16 may be used to deliver reagents such as organic additives, surfactants, ionic agents, inorganic agents or the like, which can be added to the separation microcolumn through an initial mixing step. The chemical or biochemical process conducted in the reaction chamber may be done with a separation process (carried out, for example, in an upstream microchannel in fluid communication with the reaction chamber) or a purification process (carried out, for example, in a downstream microchannel in fluid communication with the reaction chamber), in which case a number of reagents that affect selectivity and resolution may be introduced, including buffers, agents impacting solution ionic strength, agents that alter dielectric constant or viscosity, and surfactants either above or below their critical micellar concentration (CMC). Surfactants below the CMC may associate with the interior surface of the separation microcolumn and hence change the selectivity of a liquid phase separation system. Micellar formation due to the use of surfactants above the CMC may serve as a pseudo packed-column phase in a mechanism of separation known as micellar electrokinetic capillary chromatography (MEKC). Suitable surfactants for MEKC include SDS and CTAB. Additionally, chiral selectors (e.g., cyclodextrins, crown ethers, or the like) can be used to affect enhanced separation of optically active species.

A number of buffer types may be delivered from the reservoir means 16, such as, but not limited to, common organic buffers (e.g., acetate or citrate buffers), inorganic buffers (e.g., phosphate or borate buffers), or Good's buffers (e.g., MES, ACES, MOPS, CAPS, HEPES, and the like). Agents impacting solution ionic strength, such as neutral salts (e.g., NaCl, KCl, or LiCl), can alternatively be delivered from the reservoir means. Agents can also be delivered from the reservoir to affect the dielectric constant of a solution in the separation compartment. Suitable agents include common organic solvents such as, but not limited to, MeOH, EtOH, $CH_3CN$ and isopropyl alcohol. Further, a number of agents can be delivered from the reservoir means 16 to alter the viscosity of the solution passing through the separation compartment, such as methyl cellulose, dextran, polyacrylamide, polyethylene glycol, or polyvinyl alcohol. Agents which can be used in this manner to alter surface wettability include neutral surfactants (TWEEN, BRIJ or alkyl glucosides), zwitterionic surfactants (e.g., CHAPS or CHAPSO), and charged surfactants (SDS or CTAB).

The reservoir means 16 may also be used to optimize an analysis by applying increased pressure to the separation microcolumn after a solute has begun to separate. Specifically, the reservoir means can be employed to deliver a known volume of buffer to the separation microcolumn at a point after a separation has begun, thereby increasing the pressure exerted on the liquid sample.

In any of the above devices, optional means may also be provided for introducing a fluid from an external source into the reservoir compartment. Referring still to the device of FIG. 4, a fluid conducting means 28, comprising a duct laser ablated or otherwise fabricated in substrate 4, is depicted as having a first end 30 in fluid communication with the reservoir means 16. The fluid conducting means 28 has a second end 32 in fluid communication with an orifice 34 formed in the cover plate 20. Orifice 34 can comprise, for example, an aperture that has been laser ablated or otherwise fabricated in cover plate 20. Alternatively, the orifice can be positioned in the cover plate to be in direct fluid communication with the reservoir compartment. However, in each of above-described configurations, the orifice 34 allows interfacing of an external fluid source with the reservoir compartment, whereby externally contained buffers, reagents or like fluids can be introduced into the reservoir compartment for subsequent passage into the separation compartment. The external fluid source can be interfaced with the orifice through associated mechanical valving to provide a divertable fluid connection. This feature allows a variety of injection methods or other fluid introduction means to be used in order to introduce reagents or sample into the reservoir compartment via the orifice 34, including pressure injection, hydrodynamic injection or electrokinetic injection. The external valving and injection means can communicate with the orifice by butt-coupling thereto; however, any other suitable method of connection known in the art can also be used herein.

Figure 5:
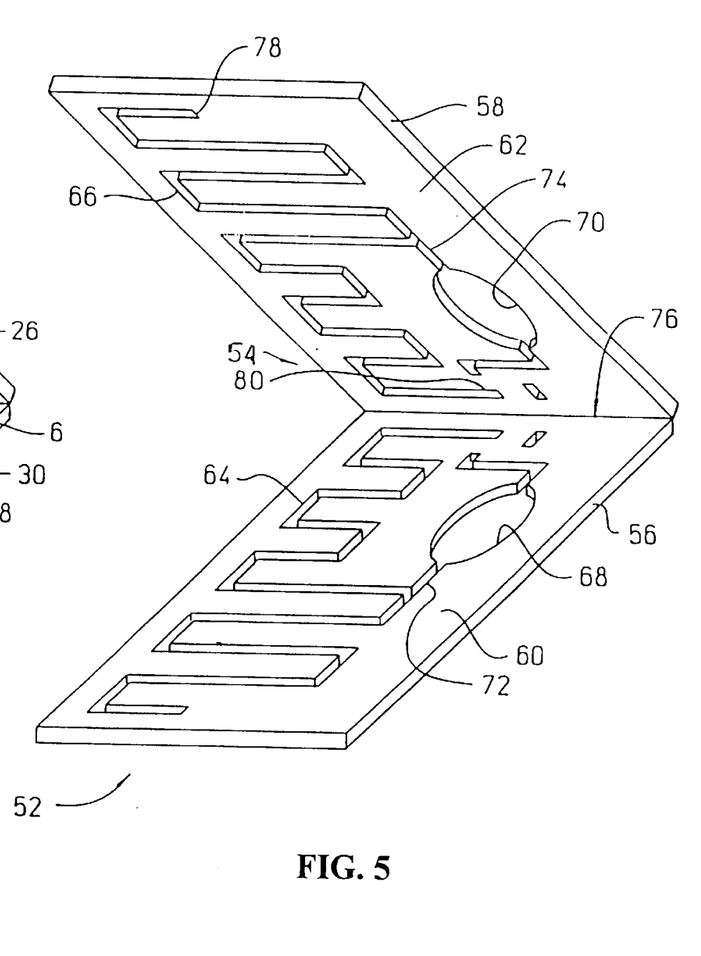
FIG. 5 is a plan view of a microreactor having an "on device" reaction chamber that is formed by the alignment of reservoir means formed on two opposing planar surfaces of a single flexible substrate.

Referring now to FIG. 5, a variation on the aforementioned microreactor is shown wherein the device is generally indicated at 52, comprising a support body 54 having first and second component halves indicated at 56 and 58 respectively. The first and second component halves, 56 and 58, each have substantially planar interior surfaces, indicated at 60 and 62 respectively, wherein high definition features can be laser ablated or otherwise fabricated. More particularly, a first microchannel pattern 64 is laser ablated or otherwise fabricated in the first planar interior surface 60 and a second microchannel pattern 66 is laser ablated or otherwise fabricated in the second planar interior surface 62. The first and second microchannel patterns in the support body 54 provide the mirror image of each other. In like manner, the column device 52 includes first and second reservoir means, 68 and 70, formed from cavities laser ablated or otherwise fabricated in the first and second planar surfaces 60 and 62, respectively, wherein the cavities provide the mirror image of each other. First and second fluid conducting means, indicated at 72 and 74, are formed from ducts laser ablated or otherwise fabricated in the first and second planar surfaces, wherein the ducts are substantially the mirror image of each other. As described above, the fluid conducting means enables fluid communication between the reservoir means and the microchannels.

The column device 52 is assembled by aligning (such as by folding) the first and second component halves 56 and 58 in facing abutment with each other. The first and second component halves are held in fixable alignment with each other to form liquid-tight separation microcolumns, reservoir compartments and fluid conducting compartments using pressure sealing techniques, such as the application of tensioned force, or by use of adhesives well known in the art of liquid phase separation devices. As described above, the first and second component halves 56 and 58 are separated by at least one fold means, generally indicated at 76, such that the halves can be folded to overlie each other. In particularly preferred devices, the fold means 76 comprises a row of spaced-apart perforations in the substrate or spaced-apart slot-like depressions or apertures extending only partway through the substrate.

The device 52 further includes means for communicating associated external fluid containment means (not shown) with the separation microcolumn (formed by the alignment of microchannels 64 and 66) to provide a liquid-phase separation device. More particularly, a plurality of apertures can be laser ablated or otherwise fabricated in the support body 54, wherein the apertures extend from at least one exterior surface of the support body and communicate with at least one microchannel, said apertures permitting the passage of fluid therethrough. More particularly, an inlet port can be laser ablated or otherwise fabricated in the second component half 58 to communicate with a first end 78 of the microchannel 66. In the same manner, an outlet port can be laser ablated or otherwise fabricated in the second component half to communicate with a second end 80 of the micro channel 66.

Accordingly, a flow path extends from the first end 78 of the micro channel 66 to the second end 80 thereof. The flow path is established by communicating fluids from an associated source (not shown) through the inlet port, passing the fluids through the separation compartment formed by the alignment of microchannels 64 and 66, and allowing the fluids to exit the separation microcolumn via the outlet port.

Figure 6:
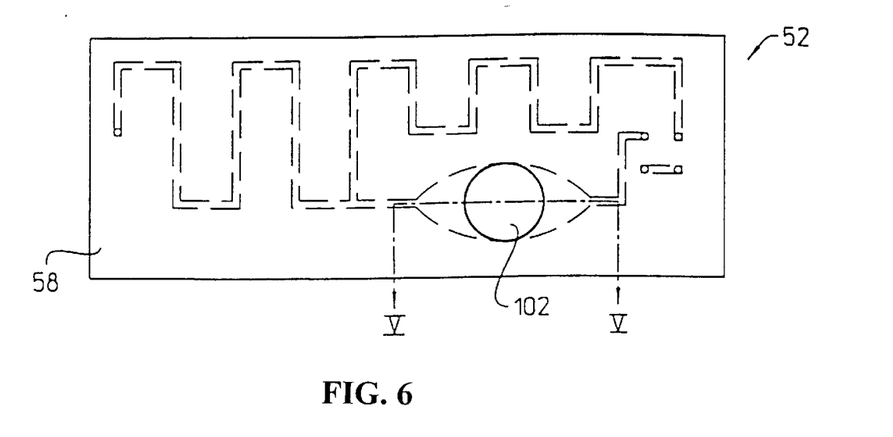
FIG. 6 is a plan view of exterior surface of a microreactor having an optional actuator means disposed over an "on-device" reaction chamber.
Figure 7:
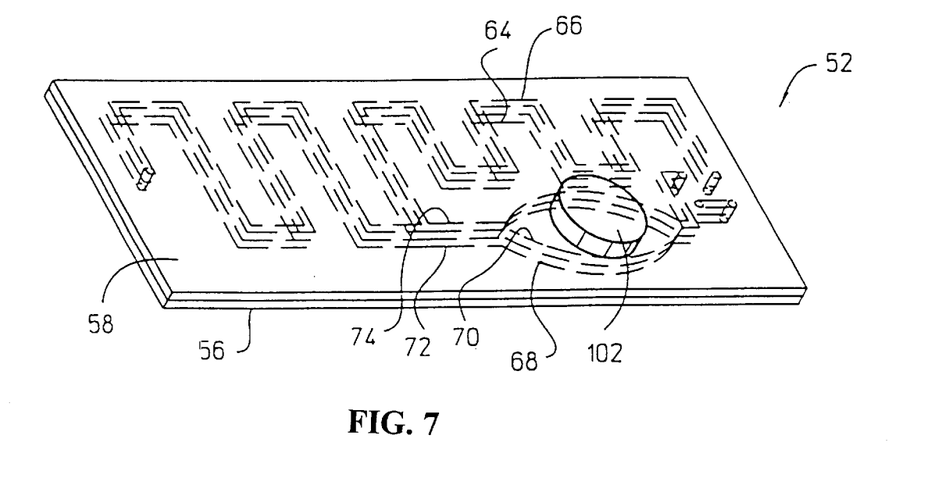
FIG. 7 is a pictorial representation of the microreactor of FIG. 6.
Figure 8:
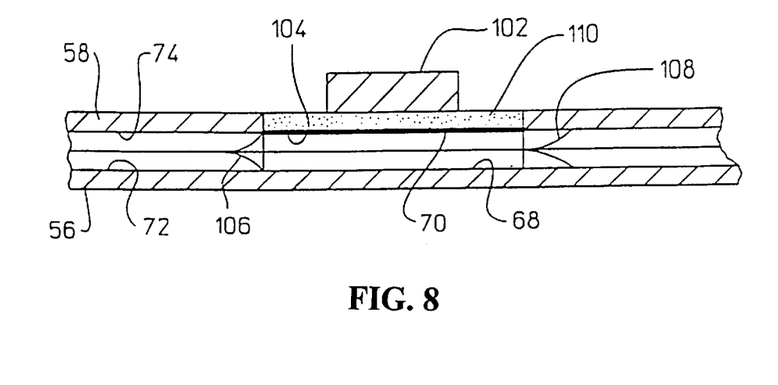
FIG. 8 is a cross-sectional view of the actuator shown in FIG. 6 taken along lines V—V and showing an optional membrane interposed between the reaction chamber and actuator means.

Optionally, the fluid may be displaced from the reservoir compartment by a motive means such as an actuator or the like. Referring to FIGS. 6–8, the microreactor 52 is depicted as including an optional actuator means 102 disposed over the reservoir compartment formed by the alignment of the first and second reservoir means 68 and 70. As best seen in the cross-sectional representation of FIG. 8, the reservoir compartment is optionally covered with thin membrane 104 to form a diaphragm-type pump. A first passive one-way microvalve 106 is optionally integrated into the fluid conducting compartment formed from the alignment of the first and second fluid conducting means 72 and 74 to prevent backflow of displaced fluid into the reservoir compartment, and a second passive one-way microvalve 108 is optionally integrated into reservoir filling means to ensure that the fluid being displaced from the reservoir compartment will travel toward the separation microcolumn.

Referring still to FIG. 8, an optional gas- or liquid-filled cavity 110 is disposed immediately above the membrane 104. The actuator means 102 can be employed to effect fluid displacement from the reservoir compartment by deflection of the membrane 104. Specifically, the actuator means 102 may act to directly deflect the membrane 104. Accordingly, the actuator means may be a piezoelectric, piston, solenoid or other type of membrane-deflecting device. Alternatively, the actuator means can be a heating means by which the temperature inside cavity 110 is regulated. The heating means can be a resistance-type heating means or any type of suitable heating means known in the art. Upon actuation, the temperature of the heating means increases, thereby heating the contents of cavity 110 and increasing the volume thereof, producing a downward deflection of membrane 104, and displacing fluid from the reservoir compartment, into the fluid conducting means past the valve 106, and into the separation microcolumn.

Alternatively, heating means 102 may be in thermal contact with the reservoir compartment itself. In this configuration, as the heating means temperature increases, the volume of the fluid in the reservoir compartment increases and is thereby displaced from the reservoir compartment into the separation microcolumn.

Other examples of pumping mechanisms which may be incorporated into the present devices include those which operate on the principles of ultrasonic-induced transport (Moroney et al. (1991) Proc MEM S'91, p. 277) or electrohydrodynamic-induced transport (Richter et al. (1991) Proc MEM S'91 p. 271). In addition, chemical valves composed of electrically driven polyelectrolyte gels (Osada (1991) *Adv. Materials* 3:107; Osada et al. (1992) *Nature* 355:242) may be used.

The use of transparent materials in the present microreactors, i.e., for the substrate and preferably the cover plate, enables use of refractive-index (RI) detection to detect separated analytes of interest passing through the separation microcolumns. For example, an associated laser diode that emits radiation at a wavelength where the device material is "transparent" allows for a detection setup where no additional features need to be provided in the devices.

Optional detection means can be included in any of the present microreactors. Referring particularly to the device of FIG. 3, one or more detection means can be laser ablated or otherwise fabricated in substrate 4 and/or cover plate 20. Preferably, the detection means will be disposed substantially downstream of the upstream terminus 12 of microcolumn 10, to enable detection of one or more components contained therein. For example, an aperture can be provided through substrate 4 to communicate with the separation channel 10. A corresponding aperture can likewise be formed in cover plate 20, and arranged so that it will be in coaxial alignment with the detection aperture in the substrate when the cover plate is affixed to the substrate. In a separation process, electrodes can be connected to the miniaturized column device via the subject corresponding apertures to detect separated analytes of interest passing through the separation compartment by electrochemical detection techniques. In one particular device configuration, the coaxially aligned apertures form an optical detection path, enabling the optical detection of separated analytes passing through the separation microcolumn via transmission of radiation orthogonal to the major axis of the separation microcolumn (and, accordingly, orthogonal to the direction of electroosmotic flow in an electrophoretic separation).

A wide variety of associated optical detection devices can be interfaced with the miniaturized columns using the optional detection means. Thus, detection of analytes in samples passing through the separation compartment can be readily carried out using UV/Vis, fluorescence, refractive index (RI), Raman and like spectrophotometric techniques.

Further, as will be readily appreciated, the use of optical detection means comprising apertures ablated into (or otherwise fabricated in) the substrate and cover plate provides great control over the effective optical detection path length. The resulting detection path length will be substantially equal to the combined thickness of the substrate 4 and the cover plate 20.

Use in PCR Amplification of DNA:

As previously discussed in the Background section, PCR is a well known and commonly used technique in the field of bioanalysis and genomics. Those skilled in the art will appreciate that the discussion of PCR methods presented herein is merely illustrative and is not intended to be limiting. DNA (Deoxyribonucleic acid) may be amplified by thermally cycling a specially constituted liquid reaction mixture according to a polymerase chain reaction (PCR) protocol that includes several incubations at different temperatures. The reaction mixture is comprised of various components such as the DNA to be amplified (the target) and at least two oligonucleotide primers selected in a predetermined way so as to be complementary to a portion of the target DNA. The reaction mixture also includes various buffers, enzymes, and deoxyribonucleotide triphosphates, such as dATP, dCTP, dGTP, and dTTP.

The reaction mixture may also include coating agents or surfactants to prevent biofouling by modifying the interior surfaces of the microreactor. Examples of such coating agents include polyethylene oxide triblock copolymers, polyethylene glycols (PEG) having molecular weights ranging from about 200 to about 8000, natural polymers such as bovine serum albumen (BSA) or any other moieties that provide the desired surface characteristics, particularly those that reduce the sorption of biomolecules such as proteins.

The duplex DNA molecule is denatured, using heat, into two complementary single strands. The primers then anneal to the strands, and nucleoside monophosphate residues are linked to the primers in the presence of a thermostable DNA polymerase to create a primer extension product. After primer extension, twice as many duplex DNA molecules exist. This process is repeated, each time approximately doubling the amount of DNA present. The result is an exponential increase in the concentration of target DNA, known as "amplification" of the target DNA. The methodology of the polymerase chain reaction is more fully described in U.S. Pat. Nos. 4,683,202 and 4,683,195.

In one embodiment of the invention, a solution having a volume in the range of about $1 \mu L$ to $500 \mu L$, preferably $10 \mu L$ to $200 \mu L$, and containing the sample to be amplified and appropriate buffers and reagents is introduced into the microreactor via any appropriate methodology. Introduction of the sample may be achieved using any convenient means, including electrokinetic injection, hydrodynamic injection, spontaneous fluid displacement and the like. The particular means employed will, for the most part, depend on the configuration of the channel as well as the necessity to introduce a precise volume of sample. For example, where the microchannel configuration employed comprises a second microchannel that intersects the first or main microchannel, the second channel can be filled with the sample and moved into the main microchannel through application of an appropriate electric field.

Once the sample fluid has passed into the reaction chamber, the microreactor is subjected to thermocycling.

The thermocycling will generally involve a denaturing step at around 93° C. to around 95° C. for 5 to 30 seconds, an annealing step at around 50° C. to around 65° C. for 2 to 20 seconds, and a polymerization step at around 72° C. for 5 to 30 seconds. The sample will generally be subjected to 30 or more cycles to produce the desired amplification. Thermocycling may be achieved by any suitable and convenient method. Commercial thermocyclers such at the RapidCycler® from Idaho Technologies and the GeneAmp 2400® form PE-Applied Biosystems are available and thermocycling may also be accomplished using a peltier plate or other heating block apparatus. Such methods and apparatus will be well known to those skilled in the art. Alternatively, thermocycling using a tungsten lamp as an infrared radiation source with cooling effected by a solenoid-gated compressed air source is also an appropriate method.

After thermocycling is complete, the microreactor is cooled to a temperature of around 4° C. and the amplified sample removed for subsequent analysis, processing, treatment or testing. The sample is removed via the outlet port and can be extracted using any convenient technique.

While the above description is illustrative of the preferred embodiments of the present invention, it will be appreciated that the microreactor in accordance with the invention may be used to practice other nucleic acid amplification and/or reaction techniques besides PCR. The above example is illustrative only. These techniques include ligase chain reaction and repair chain reaction as discussed in Abramson et al. (1993) *Current Opinion in Biotechnology* 4:41–47. The ligase chain reaction is also discussed in Barany (1991) *PCR Methods and Applications* 1:5–16. Other methods for which the invention may be used include the 3SR method discussed in Fahy et al.(1991), *PCR Methods and Applications* 1:25–33 and the Strand Displacement Assay (SDA) discussed in Walker et al.(1992) *Proc. Natl. Acad. Sci. U.S.A.* 89:392–396.

These additional techniques all involve reaction mixtures which undergo denaturation, annealing and extension processes. They primarily differ only in the specific extension mechanisms employed in the primer extension process in which the annealed oligonucleotides are extended to replicate the target strand. Repair chain reaction and LCR involve repetitive thermal cycling. 3 SR and SDA methods involve an initial denaturation step followed by an isothermal incubation for the annealing and extension processes.

Other potential applications of the above described instruments also may include cDNA synthesis prior to PCR, ligation and kinasing of DNA, and successive enzyme treatments in which reagent additions may be required during incubations or thermal cycling. Thus, the embodiments of the invention are subject to modification, variation, and change without departing from the proper scope and fair meaning of the appended claims. Accordingly, it is intended to embrace all such changes, modifications, and variations that fall within the spirit and broad scope of the appended claims. All patent applications, patents and other publications cited herein are incorporated by reference in their entirety.

Experimental

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

PCR Amplification

A GeneAmp® EZ rTth RNA PCR Kit® and the GeneAmp® rTth DNA Polymerase & EZ Buffer Pack® (PE-Applied Biosystems) were used to amplify a 308 bp DNA fragment using the method of the invention. A Master Mix of the reagents listed in Table 1 was first prepared. All reagents, except for water and PEG 8000, were obtained from the GeneAmp® EZ rTth RNA PCR Kit® and the GeneAmp® rTth DNA Polymerase & EZ Buffer Pack®. PEG 8000 was obtained from Sigma and was nuclease-free.

10 µL of the Master Mix was deposited into a 200 µm internal diameter, 12 inch Kapton® polyimide capillary tube obtained from Microlumen. The sample was loaded into the capillary tube tubing via capillary action and the ends of the capillary tube were sealed using a quick set epoxy. The tube was then inserted into 0.2 mL thin-walled PCR tube and the entire unit placed in an Idaho Technology RapidCycler® thermocycler. The sample was thermocycled using the following cycling sequence.

1. 10 minutes at 94° C.;
2. 30 seconds at 94° C.;
3. 15 seconds at 61° C.;
4. 30 seconds at 72° C.;
5. 10 minutes at 72° C.; and
6. stored until use at 4° C.

Steps 2–4 were repeated for 35 cycles.

The product was removed and stored at 4° C. A 3.5 µL aliquot of the stored product was placed in a 0.5 mL vial and 3.5 µL of 2x load buffer containing 2x SyberGreen I®(Molecular Probes) was added. The solution was incubated in the dark for 15 minutes at room temperature and amplification confirmed via agarose gel electrophoresis using a 2% NuSieve 3:1 agarose gel at 4° C. using 70V for 2 hours and 45 minutes.

TABLE 1

| Master Mix Reagents | |
|---|---|
| Component | Volume (µL) |
| Water | 19.25 |
| PEG 8000 | 3.75 |
| 5X EZ Buffer ® | 10.0 |
| dGTP | 1.5 |
| dATP | 1.5 |
| dTTP | 1.5 |
| dCTP | 1.5 |
| rTth DNA Polymerase | 2.0 |
| Mn(OAc)₂ Solution, 25 mM | 5.0 |
| Primer DM 151 | 1.5 |
| Primer DM 152 | 1.5 |
| pAW109 RNA | 1.0 |

EXAMPLES 2–7

PCR Amplification Using Pretreated Tubing

The method used in Example 1 was repeated 7 times using polyimide capillary tubing subjected to various methods of pretreatment and a 380 µm internal diameter polyethylene tube. The product produced in Example 1 and each of the products obtained using the pretreated capillary tubing and polyethylene tubing were subjected to agarose gel electrophoresis using a 2% NuSieve 3:1 agarose gel at 4° C. using 70V for 2 hours and 45 minutes. The results of the electrophoresis are presented in FIG. 9. A tabulation of the Examples, the pretreatments and the column number in FIG. 9 are presented in Table 2.

TABLE 2

Figure 9:
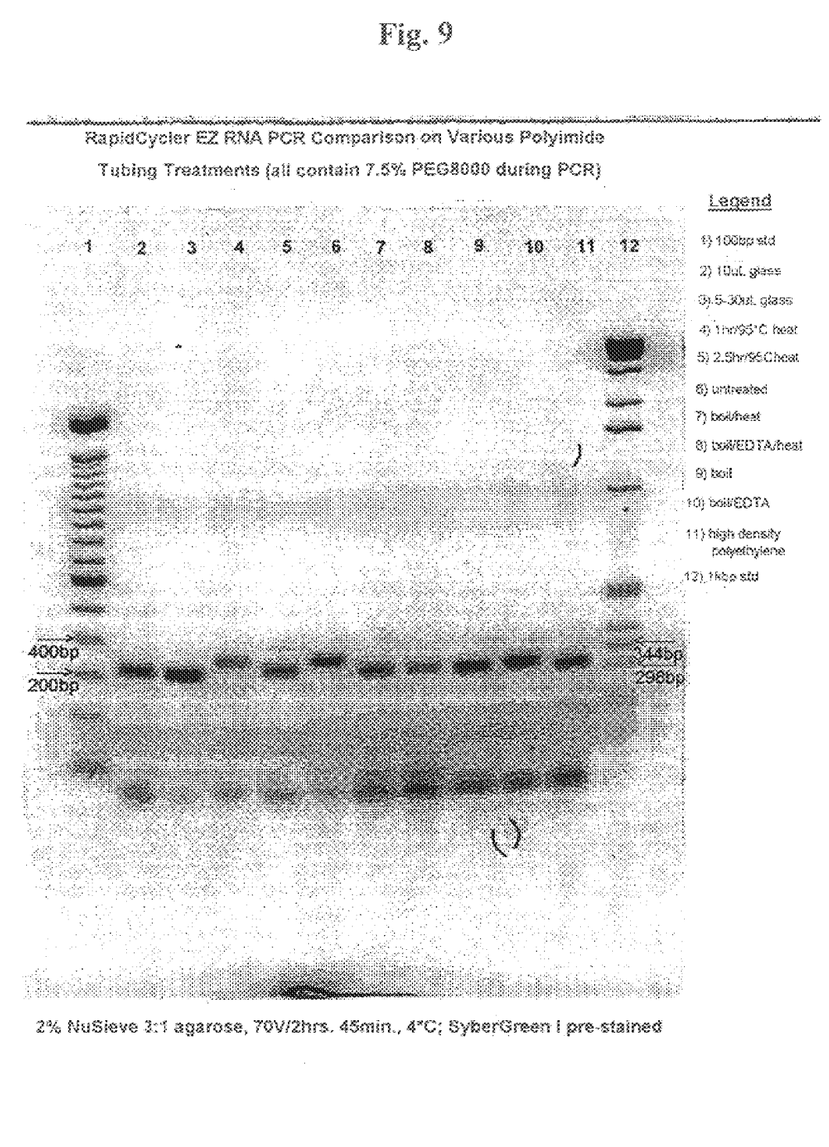
FIG. 9 is a photograph of 2% NuSieve agarose gel visualized using SyberGreenI® and UV light. This photograph demonstrates amplification of a sub-fragment of a 308-bp amplification product as described in Examples 1–8.

Example nos., Pretreatments and FIG. 9 Column Nos.

| Example Number | Pretreatment Method | FIG. 9 Col. No. |
|---|---|---|
| 1 | None | 6 |
| 2 | Heated 1 hour at 95° C. | 4 |
| 3 | Heated 2.5 hours at 950° C. | 5 |
| 4 | Boiled and Heated | 7 |
| 5 | Boiled in EDTA* and Heated | 8 |
| 6 | Boiled | 9 |
| 7 | Boiled in EDTA* | 10 |
| 8 | Polyethylene Tubing | 11 |

*ethylenediaminetetraacetic acid

EXAMPLE 9

PCR Amplification Using Bovine Serum Albumin (SBA)

The method described in Example 1 is used to amplify DNA using BSA in a 1 mg/mL concentration in the Master Mix instead of the PEG 8000.

What is claimed is:

1. In a device for conducting the polymerase chain reaction (PCR) process comprising a reaction chamber defined by two or more interior surfaces, a means for introducing PCR reaction components into the chamber, a means for removing the PCR reaction product from the chamber, and a means for controlling the temperature of the reaction chamber, the improvement which comprises:

fabricating the device from a chemically inert material that does not contain silicon and is thermally, chemically and mechanically stable under the conditions at which a PCR reaction is conducted, and employing a reaction chamber adapted to contain in the range of approximately 1 µl to 500 µl of fluid, wherein the interior surfaces of the reaction chamber are coated with a sorption-reducing polyethylene oxide layer so as to enhance thermal stability, chemical stability and biofouling resistance.

2. The device of claim 1, wherein the reaction chamber is adapted to contain in the range of approximately 10 µl to 200 µl of fluid.

3. The device of claim 2, wherein the material is selected from the group consisting of polyimides, polycarbonates, polyesters, polyamides, polyethers, polyurethanes, polyfluorocarbons, polystyrenes, poly(acrylonitrile-butadiene-styrene), polymethyl methacrylate, polyolefins, and copolymers thereof.

4. The device of claim 3, wherein the material is polyimide.

5. The device of claim 1, wherein the material is polymeric.

6. The device of claim 5, wherein the material is stable at temperatures in the range of approximately 37° C. to 94° C.

7. The device of claim 5, wherein the material has a glass transition temperature $T_g$ of at least about 100° C.

8. The device of claim 7, wherein the material has a glass transition temperature $T_g$ in the range of approximately 100° C. to 150° C.

9. The device of claim 1, wherein the material is such that high definition features may be fabricated therein.

10. The device of claim 9, wherein high definition features are present.

11. The device of claim 10, wherein the features comprise microchannels approximately 1 µm to 200 µm in diameter.

12. The device of claim 11, wherein the features comprise microchannels approximately 10 µm to 75 µm in diameter.

13. A microreactor for amplifying DNA using the polymerase chain reaction (PCR) process, comprising:

a substrate having first and second substantially planar opposing surfaces, said substrate having a cavity and at least one microchannel formed in the first planar surface, wherein the cavity serves as a reaction zone that is in fluid communication with each microchannel;

a cover plate arranged over the first planar surface, said cover plate in combination with the cavity defining a reaction chamber, and with each microchannel defining a microcolumn; and at least one inlet port and at least one outlet port communicating directly or indirectly with the reaction chamber, said ports enabling the passage of fluid from an external source into and through the reaction chamber, thereby defining a fluid flow path;

wherein the substrate and the cover plate are comprised of a chemically inert material that does not contain silicon and is thermally stable and resistant to biofouling under the conditions used for conducting PCR amplification of DNA, and the interior surfaces of the reaction chamber are coated with a sorption-reducing polyethylene oxide layer so as to enhance thermal stability, chemical stability and biofouling resistance.

14. The microreactor of claim 13, wherein the substrate material provides for reduced absorption of solutes compared to a substrate formed from a silicon-containing material.

15. The microreactor of claim 13, wherein the substrate material can be modified to alter the electroosmotic flow of a flowing fluid in contact therewith.

16. The microreactor of claim 15, wherein the reaction chamber is sized to contain approximately 1 µl to 500 µl of fluid.

17. The microreactor of claim 16, wherein the reaction chamber is sized to contain approximately 10 µl to 200 µl of fluid.

18. The microreactor of claim 17, wherein the at least one microchannel is approximately 1 µm to 200 µm in diameter.

19. The microreactor of claim 18, wherein the at least one microchannel is approximately 10 µm 75 µm in diameter.

20. The microreactor of claim 16, wherein at least one microchannel is approximately 1 µm to 200 µm in diameter.

21. The microreactor of claim 20, wherein at least one microchannel is approximately 10 µm to 75 µm in diameter.

22. The microreactor of claim 13, wherein the substrate material is polymeric.

23. The microreactor of claim 22, wherein the substrate material is selected from the group consisting of polyimides, polycarbonates, polyesters, polyamides, polyethers, polyurethanes, polyfluorocarbons, polystyrenes, poly(acrylonitrile-butadiene-styrene), polymethyl methacrylate, polyolefins, and copolymers thereof.

24. The microreactor of claim 23, wherein the substrate is comprised of polyimide.

25. The microreactor of claim 13, further including an additional cavity formed in the first planar surface, which in combination with the cover plate forms an additional reaction chamber for conducting PCR amplification of DNA.

26. The microreactor of claim 13, wherein the reaction chamber has an upstream region in which fluid is introduced and a downstream region from which fluid exits, and wherein the at least one microchannel comprises an upstream microchannel in fluid communication with the upstream region of the reaction chamber and a downstream microchannel in fluid communication with the downstream region of the reaction chamber.

27. The microreactor of claim 26, wherein the upstream microchannel in combination with the cover plate forms an upstream microcolumn, and the downstream microchannel in combination with the cover plate forms a downstream microcolumn.

28. The microreactor of claim 13, further including motive means to move fluid through the fluid flow path.

29. The microreactor of claim 28, wherein the motive means comprises a means for applying a voltage differential.

30. The microreactor of claim 28, wherein the motive means comprises a means for applying a pressure differential.

31. In a method for conducting the polymerase chain reaction (PCR) process to amplify DNA in a sample which comprises heating the sample to separate double-stranded DNA into single-stranded DNA, cooling the sample so as to allow hybridization of primer oligonucleotides to the single-stranded DNA, replicating the DNA using a DNA polymerase, and repeating the aforementioned steps to achieve the desired degree of amplification, the improvement, which comprises:

conducting the PCR in a microreactor comprised of a chemically inert material that does not contains silicon and is thermally, chemically and mechanically stable under the conditions at which the PCR reaction is conducted, and employing a reaction chamber adapted to contain approximately 1 $\mu$l to 500 $\mu$l of fluid, wherein the interior surfaces of the reaction chamber are coated with a sorption-reducing polyethylene oxide layer so as to enhance thermal stability, chemical stability and biofouling resistance.

32. The method of claim 31, wherein the reaction chamber is adapted to contain in the range of approximately 10 $\mu$l to 200 $\mu$l of fluid.

33. The method of claim 32, wherein the material is selected from the group consisting of polyimides, polycarbonates, polyesters, polyamides, polyethers, polyurethanes, polyfluorocarbons, polystyrenes, poly(acrylonitrile-butadiene-styrene), polymethyl methacrylate, polyolefins, and copolymers thereof.

34. The method of claim 33, wherein the material is polyimide.

35. The method of claim 31, wherein the material is polymeric.

36. The method of claim 31, wherein the material is stable at temperatures in the range of approximately 37° C. to 94° C.

37. The method of claim 31, wherein the material has a glass transition temperature $T_g$ of at least about 100° C.

38. The method of claim 37, wherein the material has a glass transition temperature $T_g$ in the range of approximately 100° C. to 150° C.

39. The method of claim 31, wherein the material is such that high definition features may be fabricated therein.

40. The method of claim 39, wherein high definition features are present.

41. The method of claim 40, wherein the features comprise microchannels approximately 1 $\mu$m to 200 $\mu$m in diameter.

42. The method of claim 41, wherein the features comprise microchannels approximately 10 $\mu$m to 75 $\mu$m in diameter.

43. A method for amplifying the quantity of a DNA molecule of interest contained in a small volume of sample fluid using the polymerase chain reaction process, comprising:

(a) introducing into a microreactor up to about 10 $\mu$l of a sample fluid containing the DNA molecule of interest in double-stranded form, a first and a second primer molecule complementary to opposing strands of the DNA molecule, a thermostable DNA polymerase, free deoxynucleoside triphosphates and PCR buffer, the microreactor comprising a substrate having first and second substantially planar opposing surfaces, said substrate having a cavity formed in the first planar surface, wherein the cavity serves as a reaction zone, a cover plate arranged over the first planar surface, said cover plate in combination with the cavity defining a reaction chamber, and at least one inlet port and at least one outlet port in fluid communication with the reaction chamber, said ports enabling the passage of sample fluid from an external source into and through the reaction chamber, thereby defining a fluid flow path, wherein the substrate and the cover plate are comprised of a chemically inert material that does not contain silicon and is thermally stable and resistant to biofouling, and wherein the interior surfaces of the reaction chamber are coated directly with a sorption-reducing polyethylene oxide layer so as to enhance thermal stability, chemical stability and biofouling resistance;

(b) applying a motive force to the device to move the sample fluid along the flow path into the reaction chamber;

(c) heating the sample fluid in the reaction chamber to separate the double-stranded DNA into single-stranded DNA;

(d) cooling the sample so as to allow hybridization of the primer molecules to opposing strands of the single-stranded DNA and replication of the single-stranded DNA by the DNA polymerase; and (e) repeating steps (c) and (d) to achieve the desired degree of amplification.

44. The method of claim 43, wherein the substrate material can be modified to alter the electroosmotic flow of a flowing fluid in contact therewith.

45. The method of claim 44, wherein the substrate material is polymeric.

46. The method of claim 45, wherein the substrate material is selected from the group consisting of polyimides, polycarbonates, polyesters, polyamides, polyethers, polyurethanes, polyfluorocarbons, polystyrenes, poly(acrylonitrile-butadiene-styrene), polymethyl methacrylate, polyolefins, and copolymers thereof.

47. The method of claim 46, wherein the substrate is comprised of polyimide.

48. The method of claim 43, wherein the device further includes an additional cavity formed in the first planar surface, which in combination with the cover plate forms an additional PCR reaction chamber.

49. The method of claim 43, wherein the motive means comprises a means for applying a voltage differential.

50. The method of claim 43, wherein the motive means comprises a means for applying a pressure differential.

51. A method for amplifying the quantity of a DNA molecule of interest contained in a small volume of sample fluid using the polymerase chain reaction process, comprising:
(a) introducing into a microreactor up to about 10 $\mu$l of a sample fluid containing the DNA molecule of interest in double-stranded form, a first and a second primer molecule complementary to opposing strands of the DNA molecule, a thermostable DNA polymerase, free deoxynucleoside triphosphates and PCR buffer, the microreactor comprising
  a substrate having first and second substantially planar opposing surfaces, said substrate having a cavity and at least one microchannel formed in the first planar surface, wherein the cavity serves as a reaction zone that is in fluid communication with each microchannel,
  a cover plate arranged over the first planar surface, said cover plate in combination with the cavity defining a reaction chamber, and with each microchannel defining a microcolumn, and
  at least one inlet port and at least one outlet port communicating directly or indirectly with the reaction chamber, said ports enabling the passage of sample fluid from an external source into and through the reaction chamber, thereby defining a fluid flow path,
  wherein the substrate and the cover plate are comprised of a chemically inert material that does not contain silicon and is thermally stable and resistant to biofouling, and the interior surfaces of the reaction chamber are coated with a sorption-reducing polyethylene oxide layer so as to enhance thermal stability, chemical stability and biofouling resistance;
(b) applying a motive force to the device to move the sample fluid along the flow path into the reaction chamber;
(c) heating the sample fluid in the reaction chamber to separate the double-stranded DNA into single-stranded DNA;
(d) cooling the sample so as to allow hybridization of the primer molecules to opposing strands of the single-stranded DNA and replication of the single-stranded DNA by the DNA polymerase; and
(e) repeating steps (c) and (d) to achieve the desired degree of amplification.

52. The method of claim 51, further including collecting reaction product at the outlet port.

* * * * *